(12) United States Patent
Garito et al.

(10) Patent No.: US 6,673,072 B1
(45) Date of Patent: Jan. 6, 2004

(54) RF ELECTROSURGICAL PROBE ELECTRODE WITH ADDED POINT

(75) Inventors: Jon C. Garito, Hewlett, NY (US); Alan G. Ellman, Hewlett, NY (US)

(73) Assignee: Healthcare Technologies, LLC

( * ) Notice: Subject to any disclaimer, the term of this patent is extended or adjusted under 35 U.S.C. 154(b) by 2 days.

(21) Appl. No.: 10/084,086

(22) Filed: Feb. 27, 2002

Related U.S. Application Data

(63) Continuation-in-part of application No. 09/760,522, filed on Jan. 16, 2001, now Pat. No. 6,572,613.

(51) Int. Cl.$^7$ ................................................ A61B 18/18
(52) U.S. Cl. ........................................... 606/45; 606/41
(58) Field of Search ...................... 606/41, 45, 46, 606/48–52, 167, 170, 172

(56) References Cited

U.S. PATENT DOCUMENTS

| 1,932,258 | A | * | 10/1933 | Wappler | 606/45 |
| 4,754,754 | A | * | 7/1988 | Garito et al. | 606/45 |
| 5,085,663 | A | * | 2/1992 | Tarr | 606/172 |
| 5,261,905 | A | * | 11/1993 | Doresey, III | 606/45 |
| 5,913,864 | A | | 6/1999 | Garito et al. | |
| 6,030,384 | A | * | 2/2000 | Nezhat | 606/48 |
| 6,053,912 | A | * | 4/2000 | Panescu et al. | 606/40 |
| 6,348,051 | B1 | * | 2/2002 | Farin et al. | 606/49 |

* cited by examiner

*Primary Examiner*—Michael Peffley

(57) ABSTRACT

All improved electrosurgical electrode for treating diseased tissue and lesions. The electrosurgical electrode has an active surface that may be sharpened or round. The electrosurgical electrode also has a projecting point spaced away from the active surface allowing the projecting point to be separately applied to the tissue to desiccate same.

9 Claims, 2 Drawing Sheets

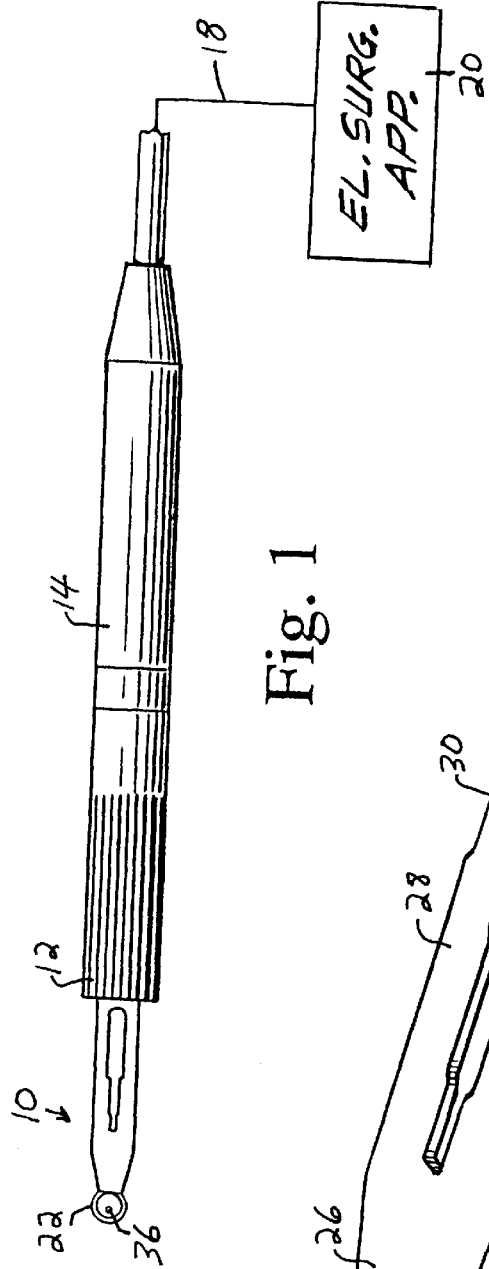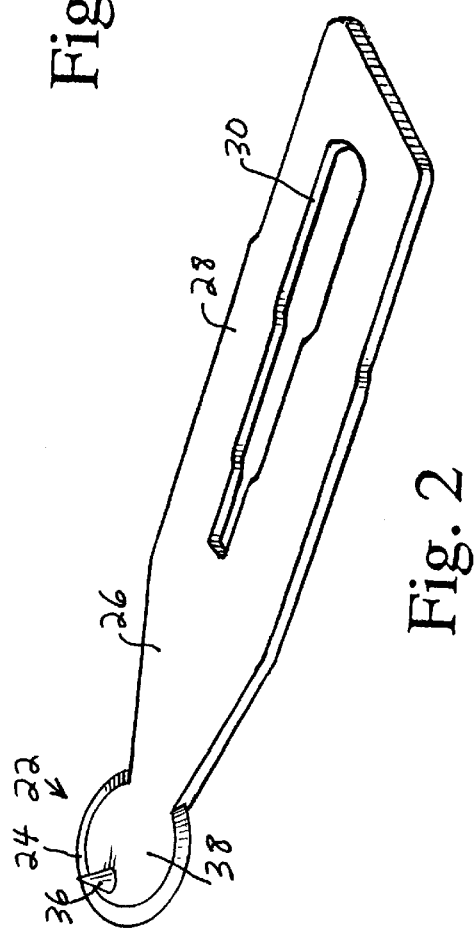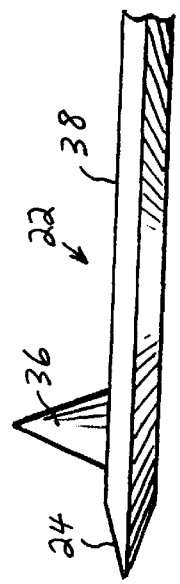

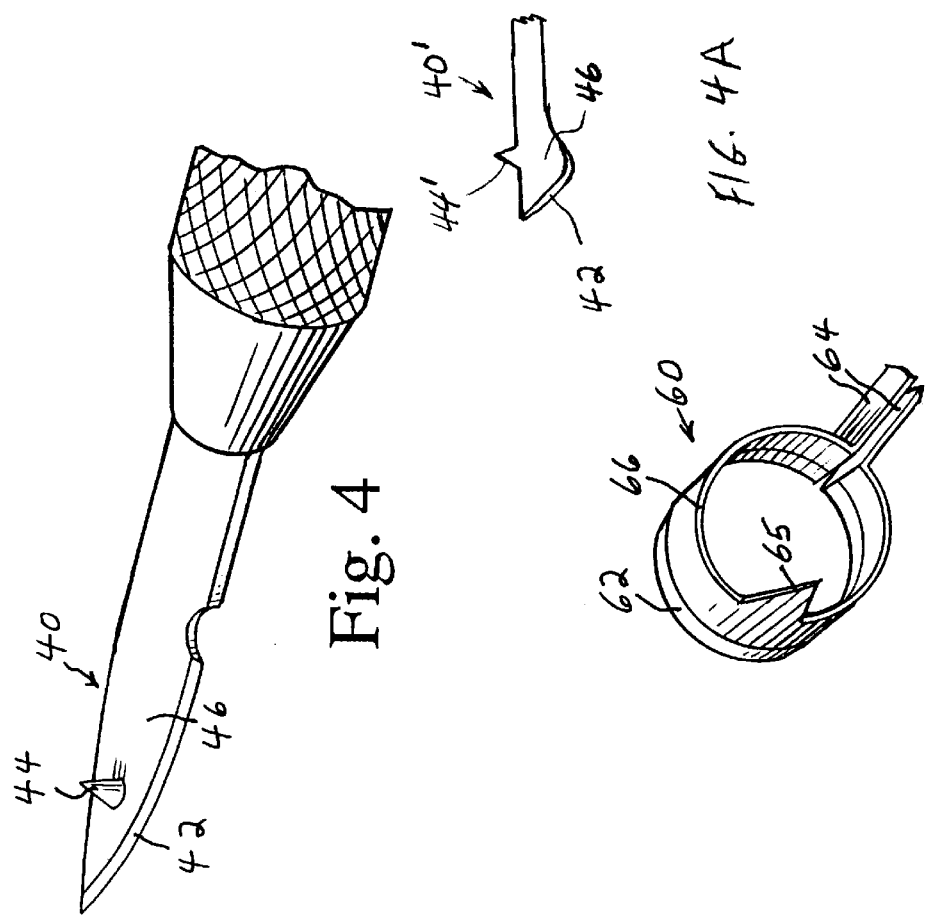

RF ELECTROSURGICAL PROBE ELECTRODE WITH ADDED POINT

RELATED APPLICATION

This application is a continuation-in-part of application Ser. No. 09/760522, filed by the same inventors on Jan. 16, 2001 now U.S. Pat. No. 6,572,613.

This invention relates to electrosurgery, and in particular to an electrode useful in desiccating lesions and tissue.

BACKGROUND OF THE INVENTION

Electrosurgery is a common procedure for dentists, doctors, and veterinarians. Electrosurgical handpieces are commercially available that will accommodate a wide variety of electrodes shapes and sizes, such as needles, blades, scalpels, balls and wire loops. Also, multi-function electrodes are available.

An electrosurgical handpiece for blades is described in U.S. Pat. No. 4,754,754, whose contents are herein incorporated by reference. This is an instrument that can be connected to a source of electrosurgical currents and that provides a slitted collet for receiving the shank of a standard disposable scalpel blade. The instrument can be used in many surgical procedures in which a conventional scalpel is employed, mainly for general cutting procedures. It has the advantage of providing electrosurgical currents at the sharp edge of the scalpel which assist in cutting tissue while at the same time providing a coagulation effect. However, the conventional scalpel blade augmented by electrosurgical currents has not been used for removing tissue and lesions using the electrodesiccation effect.

Other known electrode shapes include a curet, as described in our U.S. Pat. No. 5,913,864, whose contents are herein incorporated by reference. This is a circular band with one sharpened edge for use in an electrosurgical dermatological curretage procedure. Another shape is the well-known ball electrode which is a spherical ball on the end of an electrode shank which is used for coagulation. Still another shape is a flat round disc with a sharpened edge useful for vaporizing lesions and tumor tissue, as described in our copending application, Ser. No. 09/819,017, filed Mar. 27, 2001, whose contents are herein incorporated by reference.

The related patent application describes a probe electrode configured with an angled shape for concentrating at edges the RF energy more efficiently so as to allow a tissue reduction effect but with lowered RF voltages.

While these various shaped electrodes are suitable for their intended purposes, occasions arise from time-to-time when it would be useful to be able to use the same electrode to obtain an electrodesiccation effect, in which the RF energy instead of being supplied over a relatively wide area is concentrated into a much smaller area primarily for desiccating tissue.

SUMMARY OF THE INVENTION

An object of the invention is an improved electrosurgical electrode capable of performing cutting or coagulation with an active edge surface and can at the same time be used to destroy tissue while producing an electrodessication effect.

According to one aspect of the invention, an electrosurgical electrode comprises a flat round blade with a sharpened active edge to which a pointed projection has been added. Preferably, the pointed projection extends generally orthogonally to the plane of the blade.

According to another aspect of the invention, the electrode is formed from a standard disposable scalpel with a sharpened active edge by providing at the unsharpened edge a pointed projection. Preferably, the pointed projection extends in the plane of the blade.

According to still another aspect of the invention, the electrode is formed as an annular curette with a sharpened active edge provided at the unsharpened edge with a pointed projection. Preferably, the pointed projection extends in the plane of the curette.

According to yet another aspect of the invention, the electrode is formed as a standard ball electrode provided at a side surface with a pointed projection.

According to still another aspect of the invention, the electrode of the invention with the pointed projection is combined with electrosurgical currents at a frequency exceeding 3 MHz, preferably about 4 MHz.

The electrode of the invention is versatile, and can be used to thoroughly remove or coagulate diseased tissue with its active edge or surface and also call be used to desiccate tissue with the pointed projection.

The differently-shaped RF electrodes can be used to treat, among other items, numerous skin lesions. Examples include: warts: such as perungal warts, scalp warts, verrucae on lips, tongue, flat, digitate, filiforms warts, seborrheic warts, cordyloma acuminate, planter warts; moles: such as hairy moles, flat and slightly elevated moles, stalked pedunculated moles; melanomas: such as basel cell carcinomas; kerntoses and pre-cancerous dermatoses; leukoplakia and all skin cancers; vascalar nevi, sebaceous cysts and spider nevus. In use, the pointed projection is used to microscopically penetrate to varying depth into the diseased tissue in either of the wave form modes (cutting, coagulation) to obtain the required depth of destruction. The pointed projection is moved in a circular motion as the RF currents directed by the pointed projection destroy the diseased tissue. The result is to leave a dry base, and to seal off any bleeding vessels. All the edges and other suspicious tissue areas can be touched by the pointed projection to kill and dry-up those tissue areas.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

BRIEF DESCRIPTION OF THE DRAWINGS

In the drawings:

FIG. 1 is a plan view of one form of electrosurgical electrode according to the invention shown attached to a schematic of the handpiece described in the '754 patent which is in turn electrically connected to electrosurgical apparatus;

FIG. 2 is a top perspective view of the electrosurgical electrode of FIG. 1 separated from the handpiece. What is not shown is an electrically-insulating coating that covers the back end of the electrode as described in the copending application;

FIG. 3 is an enlarged side view of the front of the electrode of FIG. 2;

FIG. 4 is a top perspective view of another form of electrosurgical electrode according to the invention;

FIG. 4A is a top view of a variant of the embodiment of FIG. 4;

FIG. 5 is a top perspective view of yet another form of electrosurgical electrode according to the invention;

FIG. 6 is a rear perspective view of still another form of electrosurgical electrode according to the invention;

FIG. 7 is a perspective view from the front of the electrode of FIG. 6.

DETAILED DESCRIPTION OF THE PREFERRED EMBODIMENTS

U.S. Pat. No. 4,754,754 shows a handpiece of the type capable of receiving a flat blade-type of electrode such as a scalpel. The patent shows that the collet that grips the shank end of the electrode comprises a slot that can receive the flat shank end of the electrode and upon rotation in one direction can grip the electrode and upon rotation in the opposite direction can release the electrode. In the patent, the scalpel's side slot used for mounting is positioned inside of the nosepiece surrounding the collet, which is electrically-conductive, and thus no electrosurgical currents are expected to flow from the slot edges. The blade electrode of that patent, however, has different dimensions with the result that when the shank end is fitted to the collet, as depicted in FIG. 1, the portion of the blade that includes the mounting slot is located inside of the nosepiece and collet. It is of course understood that the mounting slot as such has no function in the blade electrosurgical handpiece.

FIG. 1 is a plan view of a unipolar electrosurgical electrode 10 according to the invention attached to the nosepiece 12 of the hollow handpiece 14 described in the '754 patent. The latter comprises at its end a cable 18 connected at its opposite end to a connector (not shown) for plugging into a standard electrosurgical apparatus 20 supplying electrosurgical currents to the electrode 10 having a working and 22 in the form of a flat round element whose free periphery is sharpened to form a round cutting edge 24. "Round" is used herein to mean that the working edge that is free of its support has a generally circular geometry. It will be understood that of course it cannot be a 360° circle due to the need for the shank support 26. Inside the nosepiece 12 is a collet (not shown) which receives the uncoated electrically-conductive shank end 28 of the electrode for holding the electrode within the electrosurgical handpiece 14. The cable 18 is electrically connected to the metal collet which in turn is electrically connected to the electrode 10 so that when the electrosurgical apparatus 20 is switched on, electrosurgical currents are supplied to the electrode 10. It is also common for handpiece handles to have switches (not shown) for remote operation of the electrosurgical apparatus.

The electrosurgical apparatus 20 preferably is an ultra high frequency (RF) radiosurgical energy source, which operates in the range of about 3.8–4.0 MHz. Studies have shown that the 3.8–4.0 MHz frequency range is the preferred RF energy to incise and coagulate tissue because thermal necrosis is minimal and, when interfaced with the electrosurgical electrode of the invention, provides excellent cutting and hemostasis especially for removal of cancerous tissue. An example of suitable electrosurgical apparatus is the Model SURGITRON Dual-Frequency electrosurgical unit manufactured by and available from Ellman International, Inc. of Hewlett, N.Y.

The blade electrode 10 of FIG. 1, representing a preferred embodiment of the invention, comprises a flat stamping 26 having a mounting slot 30 (not used in the invention) and which tapers to an uncoated solid circular part 38 whose periphery is sharpened to form the cutting edge 24 of the working end 22. The part of the electrode between the rear shank end 28 and the front circular part 38 is coated on both sides, including the edges, with a thin electrically-insulating coating (not shown) to prevent any electrical discharges from other than the front circular part, which typically will occur at the sharpened edge 24. The uncoated shank end 28 is buried within the handpiece and is not a likely source of electrosurgical currents. This is basically the same electrode shown and described in the copeinding application.

In accordance with the present invention, a short conical point 36 is provided near but behind the sharpened edge 24 and on the flat surface 38 of the front circular part of the active end 22. The point 36 projects approximately orthogonally upward from the flat top surface 38. It is made of the same metal as that of the working end, which typically is of stainless steel and is either formed from the blade metal or is welded to the blade metal. Preferably, the projecting point is about 0.8–4 mm high.

FIG. 4 illustrates a scalpel blade 40 as described in the '754 patent with a sharpened edge surface 42. In accordance with the present invention, a short conical point 44 is provided near but back of the sharpened edge 42 and on the flat surface 46 of the front part of the active edge 42. The point 44 projects approximately orthogonally upward from the flat top surface 46. The projecting point 44 can be made in the same manner as in the embodiment of FIGS. 1–3 and be of the same dimensions.

FIG. 5 illustrates a typical ball electrode 50 mounted on the end of a shaft 52. In accordance with the present invention, a short conical point 54 is provided on the side of the ball back of the front surface 56. The point 54 projects approximately orthogonally upward from the spherical surface 58. The projecting point 44 can be made in the same manner as in the embodiment of FIGS. 1–3 and be of the same dimensions.

FIGS. 6 and 7 are views from opposite sides of a curette electrode 60 of the type shown and described in the '864 patent. As described in the patent, the electrode 60 is made from a flat strip of metal with one sharpened edge 62 that is folded in a circle and the two free ends 64 adapted for mounting in the slitted collet of the FIG. 1 handpiece 12. In accordance with the present invention, a short planar conical point 65 is provided on the back side 66 of the curette, on the side opposite to the sharpened edge 62. The planar projecting point 65, which is in the plane of the curette strip, projects approximately orthogonally backward from the back edge 66 of the curette plane. The projecting point 65 can be made in the same manner as in the embodiment of FIGS. 1–3 and be of the same dimensions.

FIG. 4A shows a variant of the scalpel embodiment of FIG. 4. Similarly to the embodiment of FIGS. 5 and 6, the projecting point 44' is on the edge of the scalpel 40' opposite to the sharpened edge 42 and is a planar conical point that extends in the plane of the blade 46 away from the sharpened edge 42. This allows the projecting point 44' to be applied to the tissue separately from the sharpened edge 42. Again, the dimensions can be the same as those given above.

What is not shown in the drawings are the presence of electrically-insulating coatings on the conductive parts of the electrode that support the active end and that are not involved in the surgical procedure for preventing inadvertent burns to the patient.

In the operation of the embodiments of the invention, activation of the electrosurgical unit 20 causes the flow of electrosurgical currents from the electrode working end when applied against or close to the tissue to be destroyed. With the electrodes of FIGS. 2, 4 and 6, typically the sharpened edge surfaces 24, 42, 62, respectively, is used to perform a cutting operation on the tissue to be treated. Controlled vaporization and evaporation of, for example, tumor tissue can be achieved by using the sharpened blade edge especially with the 4 MHz radiofrequency apparatus. The cutting current, fully rectified waveform is used. Once the RF is applied, the knife edge blade is moved across the skin until the desired amount of tissue is vaporized. By raising the power (wattage) of the 4 MHz radiosurgery unit the greater the cutting ability and the amount of tissue destruction and vaporization over a unit period of time.

With the ball electrode of FIG. 5, typically the front spherical surface 56 is used for coagulation of bleeders when the apparatus is switched into its coagulation mode.

With all the electrodes of the invention, whenever desired, the surgeon can rearrange the orientation of the electrode, for example, by repositioning the handpiece in his or her hand, and, instead of using the sharpened edge or the ball end, can use the projecting point 36, 44, 44', 54 or 65 to desiccate tissue. This can be accomplished with the pointed projection by microscopically penetrating with the point to varying depth the tissue in either of the waveform modes (cutting, coagulation) to obtain the required depth of destruction. The pointed projection is moved in a circular motion as the RF currents directed by the pointed projection destroy the diseased tissue. The result is to leave a dry base, and to seal off any bleeding vessels. All the edges and other suspicious tissue areas can be treated in this manner after the main lesion or lesions have been excised. It will be observed that the projecting point 36, 44, 44', 54 or 65 is located in a position on each of the electrode embodiments of the invention spaced from the active edge surface such that the projecting point can be applied to tissue separately and independently from the active surface of the electrode, which in the case of the embodiments of FIGS. 2, 4, and 6 is the sharpened edge surface 24, 42, 62, and in the case of the embodiment of FIG. 5 is the front spherical surface 56.

The benefit is that the surgeon does not have to interrupt the procedure to change electrodes to perform these different tasks and risk contamination of the sterile field.

The various electrodes of the invention can be made in a variety of metals such as stainless steel, tungsten, brass, berylium and the like, stainless steel being preferred. It can be easily made in a typical and well-known stamping or welding or hard soldering operation. It can be made in a sterile disposable single use design but it is not limited to single use. It can also be made in reusable autoclaveable material.

Other variations in the shape of the electrosurgical electrode working end to which a projecting point as described can be added will provide the same or similar benefits and advantages as will be evident to those skilled in the art.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode comprising:
   a) a elongated body having an electrically-conductive first end for attaching to an electrosurgical handpiece,
   b) said elongated body having at a second end an active electrosurgical end capable of supplying electrosurgical currents when the first end is connected to electrosurgical apparatus,
   c) said active electrosurgical end comprising an active surface that is configured to perform a cutting or coagulation action when activated with electrosurgical currents and the active surface brought into contact with tissue,
   d) a projecting point on the active electrosurgical end, the projecting point being spaced away from the active surface and being located in a position such that the projecting point can be applied to tissue separately from the active surface,
   e) the active electrosurgical end comprising a scalpel blade having a flat surface and along one edge an exposed sharpened edge serving as the active surface,
   f) the projecting point being located on the flat surface of the electrode and projecting orthogonally to the flat surface of the electrode.

2. An electrosurgical electrode as set forth in claim 1, wherein the electrode is unipolar and the projecting point comprises a conical point.

3. An electrosurgical electrode as set forth in claim 2, wherein the projecting point has a height of about 0.8–4 mm.

4. An electrosurgical electrode comprising:
   a) a elongated body having an electrically-conductive first end for attaching to an electrosurgical handpiece,
   b) said elongated body having at a second end an active electrosurgical end capable of supplying electrosurgical currents when the first end is connected to electrosurgical apparatus,
   c) said active electrosurgical end comprising an active surface that is configured to perform a cutting or coagulation action when activated with electrosurgical currents and the active surface brought into contact with tissue,
   d) a projecting point on the active electrosurgical end, the projecting point being spaced away from the active surface and being located in a position such that the projecting point can be applied to tissue separately from the active surface,
   e) the active electrosurgical end comprising a curette having a curved shape and first and second edges and along the first edge an exposed sharpened edge serving as the active surface, the projecting point being located on the second edge of the electrode,
   f) the projecting point projecting orthogonally to the second edge of the electrode.

5. An electrosurgical electrode as set forth in claim 4, wherein the electrode is unipolar and the projecting point comprises a conical point.

6. An electrosurgical electrode as set forth in claim 5, wherein the projecting point has a height of about 0.8–4 mm.

7. An electrosurgical electrode comprising:
   a) a elongated body having an electrically-conductive first end for attaching to an electrosurgical handpiece,
   b) said elongated body having at a second end an active electrosurgical end capable of supplying electrosurgical currents when the first end is connected to electrosurgical apparatus,
   c) said active electrosurgical end comprising an active surface that is configured to perform a cutting or coagulation action when activated with electrosurgical currents and the active surface brought into contact with tissue,
   d) a projecting point on the active electrosurgical end, the projecting point being spaced away from the active surface and being located in a position such that the projecting point can be applied to tissue separately from the active surface, e) the active electrosurgical end comprising a generally flat round part having along a front portion of its periphery, projecting forwardly of the round part in a direction away from the first end, an exposed sharpened edge serving as the active surface, the projecting point being located on the flat round part of the electrode, f) the projecting point projecting orthogonally to the flat round part of the electrode.

8. An electrosurgical electrode as set forth in claim 7, wherein the electrode is unipolar and the projecting point comprises a conical point.

9. An electrosurgical electrode as set forth in claim 8, wherein the projecting point has a height of about 0.8–4 mm.

* * * * *